United States Patent [19]

DeLuca et al.

[11] Patent Number: 4,554,106

[45] Date of Patent: Nov. 19, 1985

[54] METHOD FOR PREPARING 1α-HYDROXYVITAMIN D COMPOUNDS

[75] Inventors: Hector F. DeLuca; Heinrich K. Schnoes; Seok H. Lee, all of Madison; Mary E. Phelps, Stoughton, all of Wis.

[73] Assignee: Wisconsin Alumni Research Foundation, Madison, Wis.

[21] Appl. No.: 667,295

[22] Filed: Nov. 1, 1984

[51] Int. Cl.$^4$ ............................................... C07J 9/00
[52] U.S. Cl. .................................................. 260/397.2
[58] Field of Search ..................................... 260/397.2

[56] References Cited

U.S. PATENT DOCUMENTS 4,022,768  5/1977  Matsunaga et al. ............... 260/397.2
4,202,829  5/1980  DeLuca et al. .................... 260/397.2
4,287,129  9/1981  Klausmeier et al. .............. 260/397.2

*Primary Examiner*—Elbert L. Roberts
*Attorney, Agent, or Firm*—Howard W. Bremer

[57] ABSTRACT

The invention relates to a process for separating 1α-hydroxyvitamin D compounds from their corresponding 1α-hydroxy-5,6-trans isomers in a mixture thereof by treating the mixture with a dienophile and then separating the resulting dienophil-adduct of the 1α-hydroxy-5,6-trans vitamin D isomer from the unreacted 1α-hydroxyvitamin D compound.

10 Claims, No Drawings

METHOD FOR PREPARING 1α-HYDROXYVITAMIN D COMPOUNDS

This invention was made with Government support under NIH Grant No. AM-14881 awarded by the Department of Health and Human Services. The Government has certain rights in this invention.

TECHNICAL FIELD

This invention relates to a novel method for the preparation of 1α-hydroxyvitamin D compounds. More specifically, the invention relates to a novel procedure for obtaining substantially pure 1α-hydroxyvitamin D compounds from mixtures containing such compounds and their corresponding 5,6-trans-vitamin D isomers.

BACKGROUND

1α-Hydroxyvitamin D compounds, specifically 1α,25-dihydroxyvitamin $D_3$ and 1α,25-dihydroxyvitamin $D_2$, are known as important regulators of calcium homeostasis and of proper bone formation in animals and humans. These compounds and certain structural analogs (e.g. 1α-hydroxyvitamin $D_3$, 1α,-hydroxyvitamin $D_2$ and related compounds) therefore find, or have been proposed for, many important uses in both human and veterinary medicine. Such uses include the prophylaxis and/or treatment of calcium metabolism disorders, such as renal osteodystrophy, rickets, osteomalacia, osteoporosis, the milk fever condition in animals, etc.

As a consequence of the medical utility of 1α-hydroxyvitamin D compounds, a variety of methods for their preparation have been developed. Summaries of these known methods have been presented, for example by Yakhimovich, Russ. Chem. Rev. 49,371 (1980), and DeLuca et al. Topics in Current Chem. vol. 83, p. 1–65 (1979), and DeLuca & Schnoes, Ann. Rev. Biochem. 52, 411 (1983).

Several of these preparatory methods for 1α-hydroxyvitamin D compounds result in mixtures of 5,6-cis and trans isomers (i.e. 1α-hydroxyvitamin D and the corresponding 5,6-trans isomer). Although for some therapeutic or other applications such mixtures may be used directly, it is generally the 5,6-cis product that is desired especially for medicinal formulations. Hence all synthetic methods yielding such cis/trans mixtures usually require separation of the isomers which is difficult and very laborious, and markedly reduces the yield of pure product.

Relevant to the present invention is specifically the 1α-hydroxylation method via 3,5-cyclovitamin D intermediates, as described in U.S. Pat. Nos. 4,195,027 and 4,260,549. In this method the C-3-hydroxy group of a vitamin D compound is tosylated, and the tosylate is subjected to solvolysis to obtain a 3,5-cyclovitamin intermediate. This intermediate is then oxidized to the 1α-hydroxycyclovitamin compound and the latter is solvolyzed to obtain a mixture of the 5,6-cis and 5,6-trans-1α-hydroxyvitamin D compounds (usually as the 3-acetate derivatives). Whenever, for pharmaceutical use, the 5,6-cis compound is the desired product, the cis/trans mixture resulting from solvolysis must be separated.

Also relevant is the method of Salmond, U.S. Pat. No. 4,206,131, for the preparation of 1α-hydroxyvitamin D compounds. In this procedure, 1α-hydroxy-5,6-trans-vitamin D compounds are produced as intermediates, which are then isomerized to the desired 5,6-cis vitamins. Since known isomerization methods result in mixtures of cis and trans vitamin D compounds, separation of the desired cis-product from the mixture is again required. Similarly, the 1α-hydroxylation methods proposed in U.S. Pat. Nos. 4,202,829, 4,263,215, 4,265,822, and 4,338,250, which involve direct 1-hydroxylation of 5,6-trans-vitamin D compounds, followed by 5,6-double bond isomerization, require, if the pure cis product is desired, methods for the separation of the 5,6-cis compound from the cis/trans mixture.

Because of the very similar chromatographic properties of the cis and trans isomers, such separation, though feasible, on a small scale with efficient columns, is very difficult, laborious and expensive, especially on a preparative scale. This difficulty in separating cis and trans isomers is thus a major disadvantage of the above methods.

DISCLOSURE OF INVENTION

A new method for the preparation of 5,6-cis-1α-hydroxyvitamin D compounds has now been found which allows for the effective and efficient removal of 5,6-trans-1α-hydroxyvitamin D compounds from mixtures of the 5,6-cis- and trans-isomers so as to obtain the desired 5,6-cis-vitamin D isomer in substantially pure form. Specifically, this novel method comprises treatment of a mixture of 5,6-cis- and trans-1α-hydroxyvitamin D compounds with a dienophile under reaction conditions so chosen as to produce selectively the Diels-Alder adduct of the 5,6-trans-vitamin D compound. The resulting mixture of unreacted 5,6-cis-vitamin D compound and the Diels-Alder adduct of the 5,6-trans-vitamin D compound is now readily separated in a chromatographic or extractive step.

The purpose of the reaction with the dienophile is thus to convert the two chromatographically very similar constituents of the mixture, the 5,6-cis and trans-vitamin D compounds, into a mixture of two chemically and chromatographically very different components, the adduct of the trans-compound and the unreacted 5,6-cis-vitamin, from which the adduct is readily removed so as to obtain the desired 5,6-cis-vitamin D compounds in substantially pure form.

The 5,6-cis and 5,6-trans vitamin D compounds, the mixture of which may be separated by the above summarized procedure, are characterized by the formulae shown below:

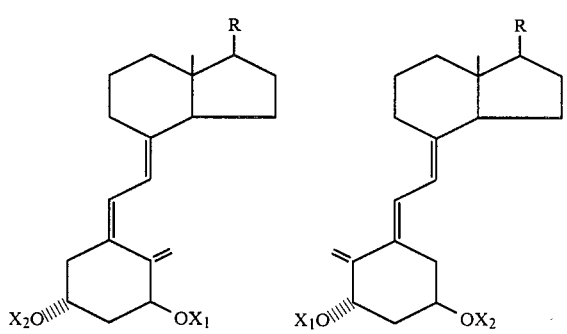

where $X_1$ and $X_2$ represent, independently, hydrogen or a hydroxy-protecting group, and where R may be any steroid side chain, e.g. R may be hydrogen or an alkyl radical, or R may be a substituted side chain of the type

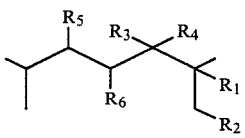

wherein $R_1$, $R_2$ and $R_3$ are each selected from the group consisting of hydrogen, hydroxy, halogen and protected hydroxy, $R_4$ is hydrogen, halogen or alkyl, and $R_5$ and $R_6$ are selected, independently, from hydrogen, hydroxy, and protected hydroxy, or taken together, may form a carbon-carbon double bond.

In this specification and in the claims, a hydroxy-protecting group represents any of the groups well known in the art used for the temporary protection of hydroxy functions, such as an acyl group, an alkylsilyl group, or an ether group. A protected hydroxy is thus a hydroxy function derivatized (i.e. acylated, etherified) with one of these protecting groups. An acyl group is an alkanoyl group of 1 to 6 carbons, in all isomeric forms, e.g. formyl, acetyl, propionyl, butyryl, pivaloyl etc., or an aroyl group, such as benzoyl, or an alkyl-, halo- or nitro-substituted benzoyl group. Suitable alkylsilyl hydroxy-protecting groups are for example, trimethylsilyl, triethylsilyl, t-butyldimethylsilyl and analogous alkyl-substituted silyl-radicals. Suitable ether protecting groups are methoxymethyl or ethoxymethyl groups, or tetrahydrofuranyl or tetrahydropyranyl groups, all of which are well-known in the art. The term "alkyl" signifies a hydrocarbon radical of from 1 to 6 carbons, in all its isomeric forms, e.g. methyl, ethyl, propyl, isopropyl, butyl, etc. The term "aryl" signifies a phenyl group or an alkyl-, halo-, or nitro-substituted phenyl group.

The key aspect of the separation of a mixture of cis and trans vitamin D compounds is the treatment of such a mixture with a reactive dienophile. Although both 5,6-cis and trans vitamin D compounds can react with dienophiles, the 5,6-trans compounds undergo the reaction more rapidly, so that, under some conditions treatment of a mixture of cis and trans compounds with a dienophile, will yield almost exclusively the Diels-Alder adduct of the trans-isomer, while the cis-compound remains unaltered.

Suitable dienophiles for the above application are olefinic, acetylenic, or diazene compounds, characterized, respectively, by the general structures below

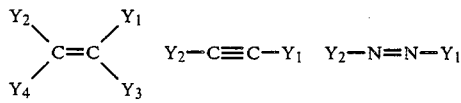

wherein each of the substituents $Y_1$ $Y_2$, $Y_3$, and $Y_4$ is selected from the group consisting of hydrogen, alkyl, and an electron-withdrawing group, and where any two of the Y-substituents taken together may form a carbocyclic or heterocyclic ring, but where, in each case, at least one of the substituents Y is an electron-withdrawing group. An electron-withdrawing group, in the context of this invention, is a group which activates the dienophile towards reaction with a diene. Such activating groups are well-known in the art (see, for example, M. C. Kloetzel, Organic Reactions, vol. 5, p. 2-4; H. L. Holmes, Organic Reactions, vol. 5, p. 65) and include, for example, such groupings as keto, cyano, nitro, O-alkyl, O-acyl, halogen, aryl, carboxyaldehyde, carboxylic acid, alkyl carboxylate, carboxamide, or the imide, or anhydride-form of a dicarboxylic acid.

Specific examples of suitable dienophiles are: acrylic acids and alkyl esters thereof, acrylamide and acrylonitrile; acetylenic acids and esters, such as propiolic acid and its alkyl esters, or acetylene dicarboxylic acid and its mono- or di-alkyl esters; maleic acid and its derivatives, such as maleic anhydride, maleimide, N-substituted maleimides, and maleic acid mono-or di-alkyl esters; quinones such as benzoquinone or naphthoquinone; and diazene-dienophiles such as N(4)-alkyl- or N4-aryl-substituted triazoline-3,5-dione, diazo-p-benzoquinone, diazo-p-naphthoquinone, or the alkyl esters of azodicarboxylic acid.

For work on larger scale, dienophiles such as maleic acid and its derivatives, e.g. maleic anhydride, are particularly useful because of their low cost, and the possibility of removing the resulting adducts from the mixture by hydrolytic/extractive work-up (as described below). Other preferred dienophiles include acetylene dicarboxylic acids and esters, and N(4)-alkyl or phenyl substituted triazoline-3,5-diones. The diazo-p-benzoquinone or diazonaphthoquinone dienophiles, although also useful for purposes of the present invention, because of their extremely high reactivity require conducting the reaction at exceedingly low temperatures to achieve discrimination in adduct formation between cis and trans vitamin D compounds, offer less advantage.

The reaction of the above dienophiles with the cis-/trans vitamin D mixture is conducted by adding the dienophile to the vitamin mixture in an organic solvent. It should be noted that in such a mixture the 5,6-cis and trans vitamin D compounds can be present in any proportion relative to each other.

To assure complete reaction of the trans-vitamin the dienophile reagent is added in a 1.5-5-fold excess over the known (or estimated) amount of 5,6-trans compound present. Suitable solvents are hydrocarbons, chlorinated hydrocarbons, low-molecular weight ethers, or low molecular weight acid or ester solvents; specific examples include, benzene, hexane, toluene, chlorobenzene, ethyl ether or ethyl acetate. As pointed out above, the dienophile is advantageously added in about 1.5-5-fold excess over the amount of 5,6-trans compound estimated to be present. The reaction can be conducted over a wide temperature range, e.g. from about −50° C. to the boiling temperature of the solvent used, and for a time sufficient to react all of the 5,6-trans-compound present. The specific temperature and time chosen depends on the reactivity of the dienophile. For highly reactive dienophiles, temperatures in the lower part of the range indicated are appropriate, for the less reactive ones the upper temperature range is preferred. The time required for the reaction also depends on the reactivity of the dienophile, and varies from minutes to hours.

For example, for the reaction of a cis/trans vitamin D mixture with the reactive dienophile 4-phenyl-triazoline-3,5-dione, suitable reaction conditions are a temperature of 0°-10° C., for 1-2 hr, using ca. 2-3-fold excess of reagent. For the reaction of a cis/trans vitamin mixture with maleic anhydride, a somewhat less reactive reagent, appropriate conditions are, a temperature of 30°-40° C., for ca. 12-24 hr, using a 4-fold excess of the dienophile. At higher temperatures, e.g. 50°-60° C. the reaction is complete within 1-2 hrs and at about 80° C., a reaction time of 10-20 min. is appropriate. In general, 1α-hydroxyvitamin D compound is recovered, and if required, further purified.

It will be noted that the above method for preparing 1α-hydroxyvitamin D compounds can be usefully applied to any mixture of the 5,6-cis- and trans-isomers, regardless of the synthetic origin of such mixtures. The new method is particularly useful for those cases where the direct separation (e.g. by chromatography) of 5,6-cis- and trans-isomer mixtures is especially difficult. Such is true, for example, whenever the substituents $X_1$ and $X_2$ in the above-shown structures of 5,6-cis and trans compounds are alike or very similar (e.g. $X_1$ and $X_2$ are both hydrogen or both acyl). In addition, it is evident that the new method can be applied advantageously in all preparative work conducted on a large (e.g. commercial) scale. It is also obvious that, if required, the above described separation procedure using dienophiles can be repeatedly applied to the same preparation. If for example, the 1α-hydroxyvitamin D product obtained by the process of this invention is found to still contain some residual undesired 5,6-trans-isomer (as might occur, for example, if reaction time was insufficient), this product may simply be treated again with the same or a different dienophile, according to the above procedure, to remove such undesired residual material.

EXAMPLE 1

A mixture (1 g) of 5,6-cis- and 5,6-trans-1α-hydroxyvitamin $D_3$ (containing about 20–25% of the trans compound) dissolved in ethyl acetate (25 ml) was treated with recrystallized maleic anhydride (4-fold molar excess over the 5,6-trans-vitamin compound present) and warmed to 35° C. under nitrogen for 24 hr. The solvent was then removed under vacuum and 10% aqueous NaOH (25 ml) was added to hydrolyze the anhydride adduct of the 5,6-trans compound. After 15 minutes the mixture was extracted with ether and the ether extracts were washed with 10% NaOH, water and brine and then dried over $MgDO_4$. The solvent was removed in vacuo and the resulting residue was applied to a silica gel column (2×30 cm) and product was eluted with ethyl acetate/hexane mixtures (500 ml of 10% ethyl acetate; then 500 ml of 30% and 500 ml of 50% ethylacetate in hexane). The fractions containing the desired 1α-hydroxyvitamin $D_3$ were pooled, solvent was evaporated, and a portion of the resulting oil was crystallized from methyl formate. After two recrystallizations from the same solvent crystalline 1α-hydroxyvitamin $D_3$, mp 135°–37° was obtained.

EXAMPLE 2

A mixture (0.75 g) of 1α-hydroxyvitamin $D_3$ 3-acetate and 1α-hydroxy-5,6-trans-vitamin $D_3$ 3-acetate (containing about 30% of the trans isomer), was dissolved in 25 ml of ethyl acetate and treated with excess maleic anhydride (ca. 4-fold molar excess over the estimated amount of 5,6-trans isomer present). After 24 hr at 35° C., the solvent was removed in vacuo, 10% aqueous sodium hydroxide (25 ml) was added and the mixture was stirred for 10–20 min to saponify the anhydride adduct of the 5,6-trans-compound. (This saponification also removes the acetyl groups.) This mixture, transferred to a separatory funnel, was then extracted repeatedly with ether, and the combined ether extracts were washed with 10% aqueous NaOH, water, and saturated NaCl-solution and then dried ($MgSO_4$). The solvent was evaporated to obtain the desired 1α-hydroxyvitamin $D_3$ product which was purified by chromatography on a silica gel column (eluted with ethyl acetate/hexane mixtures) and then by preparative TLC (50% ethyl acetate/hexane) to yield 290 mg of 1α-hydroxyvitamin $D_3$.

EXAMPLE 3

A mixture (840 mg) of 5,6-cis and trans 1α-hydroxyvitamin $D_3$ (containing ca. 20–25% trans compound) in 10 ml ethyl acetate was treated with 820 mg of maleic anhydride under $N_2$ at 55° C. for 90 min. Solvent was evaporated, the residue was treated with aqueous NaOH (20 min., room temperature) and then the mixture was extracted repeatedly with ether; the organic phase was washed with $H_2O$, and saturated NaCl solution, then dried over $MgSO_4$, filtered and solvent was evaporated. The residue (comprising the desired 1α-hydroxyvitamin $D_3$ compound) was chromatographed on a 3×27 Florisil column. After passage of 300 ml of 15% ethyl acetate in hexane, the product (1α-hydroxyvitamin $D_3$) was eluted with 25% ethyl acetate in hexane. Evaporation of solvent gave 440 mg of colorless oil, which was crystallized from methyl formate to give crystalline 1α-hydroxyvitamin $D_3$ product.

EXAMPLE 4

An ca. 1:1 mixture of 1α-hydroxyvitamin $D_3$ 3-acetate and 1α-hydroxy-5,6-trans-vitamin $D_3$ 3-acetate was dissolved in hexane and treated with a 1.5-fold molar excess (over the trans-compound present) of 4-phenyltriazoline-3,5-dione (1 mg/ml as solution in ethyl acetate). The resulting mixture was allowed to react at 0°–10° C. for 65 min. Excess reagent was consumed by addition of isoprene, and the mixture was then directly chromatographed to obtain 1α-hydroxyvitamin $D_3$ in pure form.

We claim:

1. A method for preparing 1α-hydroxyvitamin D compounds which comprises treating a mixture containing said compounds and their corresponding 1α-hydroxy-5,6-trans-vitamin D isomers, with a dienophile, whereby a mixture containing the dienophile-adduct of the 1α-hydroxy-5,6-trans-vitamin D isomer and the unreacted 1α-hydroxyvitamin D compound is obtained, and separating said mixture.

2. The method of Claim 1 wherein the dienophile is selected from the group consisting of maleic acid, maleic acid mono alkyl ester, maleic acid di-alkyl ester and maleic anhydride.

3. The method of Claim 1 wherein the dienophile used is acetylene dicarboxylic acid, or an alkyl-or dialkyl ester thereof.

4. The method of Claim 1 wherein the dienophile is a 4-alkyl- or 4-aryl-triazoline-3,5-dione compound.

5. The method of Claim 1 wherein the desired 1α-hydroxyvitamin D compound is separated from the adduct of the 5,6-trans isomer by chromatography.

6. The method of Claim 2 or 3 wherein the desired 1α-hydroxyvitamin D compound is separated from the adduct of 5,6-trans-vitamin D isomer by treatment of the mixture with an alkaline metal hydroxide and partioning between an aqueous and organic solvent medium whereby the 1α-hydroxyvitamin D compound can be recovered from the organic solvent.

7. The method of Claim 1 wherein the cis/trans vitamin D mixture contains 1α-hydroxyvitamin $D_3$ and 1α-hydroxy-5,6-trans-vitamin $D_3$.

for any given dienophile, appropriate reaction conditions (e.g. time and temperature) are easily determined by simply treating a small test sample of a cis/trans vitamin D mixture with the dienophile and checking the progress of the reaction (i.e. completeness of reaction with the trans-compound) by analysis of the reaction mixture (e.g. by thin layer or high performance liquid chromatography). Obviously, unduly prolonged reaction of a cis/trans vitamin D mixture with a dienophile is to be avoided to prevent losses of the desired 5,6-cis-vitamin D compound owing to its reaction (adduct formation) with the dienophile.

After treatment with the dienophile, the reaction mixture consists of the Diels-Alder adduct of the 5,6-trans compound and the unreacted 5,6-cis compound, as represented by the structures below,

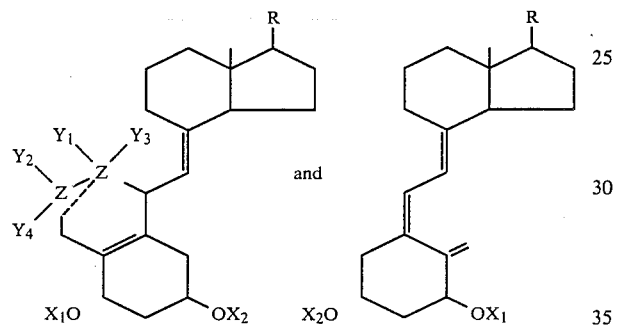

where R and $X_1$ and $X_2$ represent substituents as defined above, where Z represents carbon or nitrogen, which may be joined by a single or double bond, depending on the dienophile used in the reaction, and where $Y_1$, $Y_2$, $Y_3$ and $Y_4$ each have the meaning as defined above, except that when Z is nitrogen, or double-bonded carbon, $Y_3$ and $Y_4$ will be absent, as is self-evident to one skilled in the art.

For example, the reaction of the 5,6-trans compound with maleic anhydride, dimethyl acetylene dicarboxylate and 4-phenyltriazoline-3,5-dione, respectively, yields the adducts characterized, respectively, by the structures shown below:

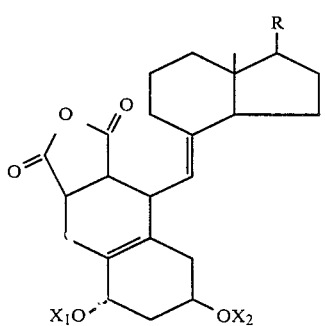

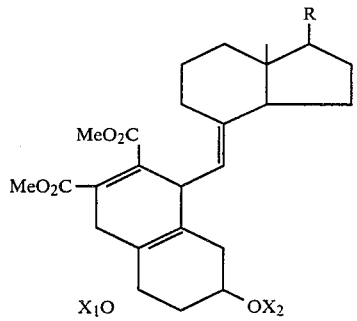

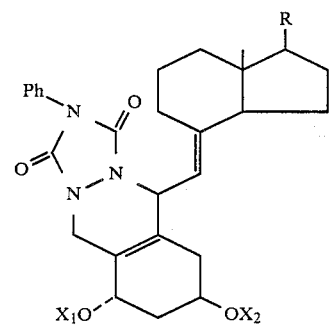

Unlike the free 5,6-trans compounds which are chromatographically very similar to the 5,6-cis isomers, the Diels-Alder adducts of the trans compounds, as is readily apparent from inspection of the above structures, are substantially altered and thus behave very differently from the free 5,6-cis compounds on chromatography. Therefore, such adducts are readily separated by chromatography from the free 5,6-cis-compounds, e.g. on silica gel columns, or by preparative high pressure liquid chromatography. Even more advantageous, especially for large-scale preparations, is the separation of the adduct from the free 5,6-cis vitamin compound by simple solvent extraction. This is possible whenever the dienophile used in the above Diels-Alder reaction contains an acidic function (e.g. a phenolic or acid function), or a function, such as ester or anhydride, that is readily saponifiable to a carboxylate group. The 5,6-trans-vitamin-adduct can then be removed from the 5,6-cis-vitamin by extraction of the organic phase with dilute base. For example, treatment of a cis/trans vitamin D mixture with maleic anhydride yields a mixture of the free 5,6-cis-vitamin D compound and the maleic anhydride adduct of the 5,6-trans compound. This reaction product mixture can then be treated with aqueous alkali metal hydroxide (e.g. NaOH or KOH) to saponify the anhydride adduct to the corresponding dicarboxylate. The resulting adduct-dicarboxylate derivative, being water-soluble, is then easily separated from the organic-soluble 5,6-cis-1α-hydroxyvitamin D compound by simple partitioning of the basic solution against an immiscible organic solvent and separation of the phases. The desired 1α-hydroxy-5,6-cis-vitamin product, retained in the organic phase, is then isolated by evaporation of the solvent, and if required, further purified in the customary fashion, i.e. chromatography and/or crystallization. Alternatively, the undesired 5,6-trans-vitamin D adduct carboxylate can be removed from the free 1α-hydroxyvitamin D compound by treatment of the mixture with (or passage over) an ion exchange resin in the standard manner, whereby the free 8. The method of Claim 1 wherein the cis/trans vitamin D mixture contains 1α-hydroxyvitamin $D_2$ and 1α-hydroxy-5,6-trans-vitamin $D_2$.

9. The method of Claim 1 wherein the cis/trans vitamin D mixture contains 1α,25-dihydroxyvitamin $D_3$ and 1α,25-dihydroxy-5,6-trans-vitamin $D_3$.

10. The method of Claim 1 wherein the cis/trans vitamin D mixture contains 1α,25-dihydroxyvitamin $D_2$ and 1α,25-dihydroxy-5,6-trans-vitamin $D_2$.

* * * * *